United States Patent [19]

Hervas

[11] Patent Number: 4,962,877

[45] Date of Patent: Oct. 16, 1990

[54] HYDRAULIC DEVICE WITH FLEXIBLE BODY FOR SURGICAL ANASTOMOSTS

[76] Inventor: Pedro L. Hervas, Paseo Santa Maria de la Cabeza 17, 28045 Madrid, Spain

[21] Appl. No.: 400,493

[22] Filed: Aug. 30, 1989

[30] Foreign Application Priority Data

Sep. 2, 1988 [ES] Spain .................................. 8802719

[51] Int. Cl.⁵ .............................................. A61B 17/00
[52] U.S. Cl. ..................................... 227/179; 227/180
[58] Field of Search .............................. 606/175–181; 227/19, 179, 180

[56] References Cited

U.S. PATENT DOCUMENTS 4,485,817 12/1984 Swiggett ......................... 128/334 R
4,488,523 12/1984 Shichman ....................... 128/334 R Primary Examiner—Randall L. Green
Assistant Examiner—Gary Jackson
Attorney, Agent, or Firm—Ladas & Parry

[57] ABSTRACT

A hydraulic device, depending for performing mechanical anastomoses within the field of surgery, consisting of a head which sutures the ends to be anastomized by means of metal staples, hydraulically operated by means of plungers; a flexible body consisting of hydraulic conducting tubes which can be bent to allow anastomoses to be carried out in anatomical locations with difficult access for currently used rigid systems; and a control system which operates the fluid driving the head mechanisms; provided with a valve system to ensure proper stapling.

11 Claims, 3 Drawing Sheets

HYDRAULIC DEVICE WITH FLEXIBLE BODY FOR SURGICAL ANASTOMOSTS

BACKGROUND OF THE INVENTION 1. (Field of the Invention)

The invention refers to a device for performing mechanical sutures, hydraulically operated and provided with a flexible body, mainly intended for application to intestinal anastomosis in the course of abdominal surgery.

2. (Description of Prior Art)

For a number of years now there have been available on the market mechanical suture devices, with a choice of several different models. For circular sutures of the type known as termino-terminal or latero-terminal, there exist devices which suture by means of metal staples the ends which need to be anastomized.

To this end, said ends are knotted around a metal shaft on the suturing head, straight after which both ends are brought close to each other until good contact has been established; next, the stapling mechanism is brought into operation, whereby the U-shaped metal staples are pushed and forced through the tissue to a sutured, and the staple ends are bent inwards against a support head, folding the staples into a B-shape. Simultaneouosly, a cylindrical blade cuts off the part of the knotted tissue to the inside of the staples, thereby restoring a clear passage in the anastomosis.

Such devices are driven by rigid shafts, with a set of mechanisms which constitute a rigid system from the head to the control mechanism. This constitutes a drawback in terms of the possibilities of access of the device to the field of surgery, since in many cases it is necessary to perform anastomosis in deep and narrow locations.

SUMMARY OF THE INVENTION

These disadvantages are done away with by means of the hydraulic device with flexible body for surgical anastomosis introduced by the present invention. Such a device still achieves the suture between the ends by means of conventional metal staples, but the rod-driven mechanism is replaced by a hydraulic system in which the body is made up of flexible tubes which carry the driving fluid which will activate the approximation, stapling and cutting of the tissues to be anastomized, and due to the flexibility of the body the device can describe curves in space, thus enabling the suturing head to reach locations inaccesible in the case of the rigid system, anatomic path up to the place of action.

The hydraulic device with flexible body therefore constitutes a significant technological breakthrough in this field.

BRIEF DESCRIPTION OF THE DRAWINGS

As an aid to the understanding of the characteristics of the present invention, a detailed description will be given, based on the set of drawings enclosed with the present descriptive report, which drawings are a constituent part of said report, and feature, for purposes of information rather than a restrictive description, the following.

DETAILED DESCRIPTION

Figure 1:
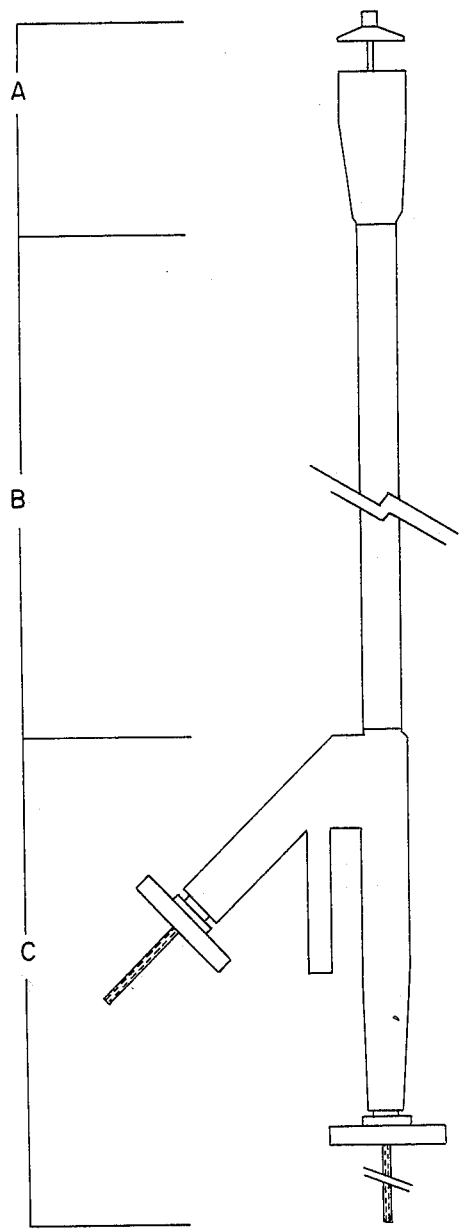
FIG. 1 is a front view of the invention, which contains three main parts labelled A,B,C, which correspond to the suturing and cutting head, flexible body and controls system respectively.
Figure 2:
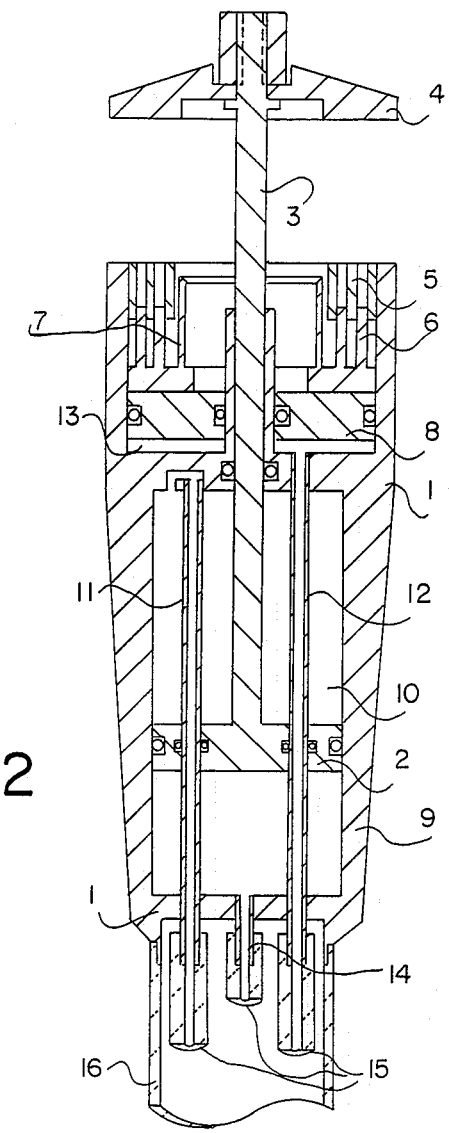
FIG. 2 is a longitudinal section of the part corresponding to the head A, and the first part of the flexible body B.
Figure 3:
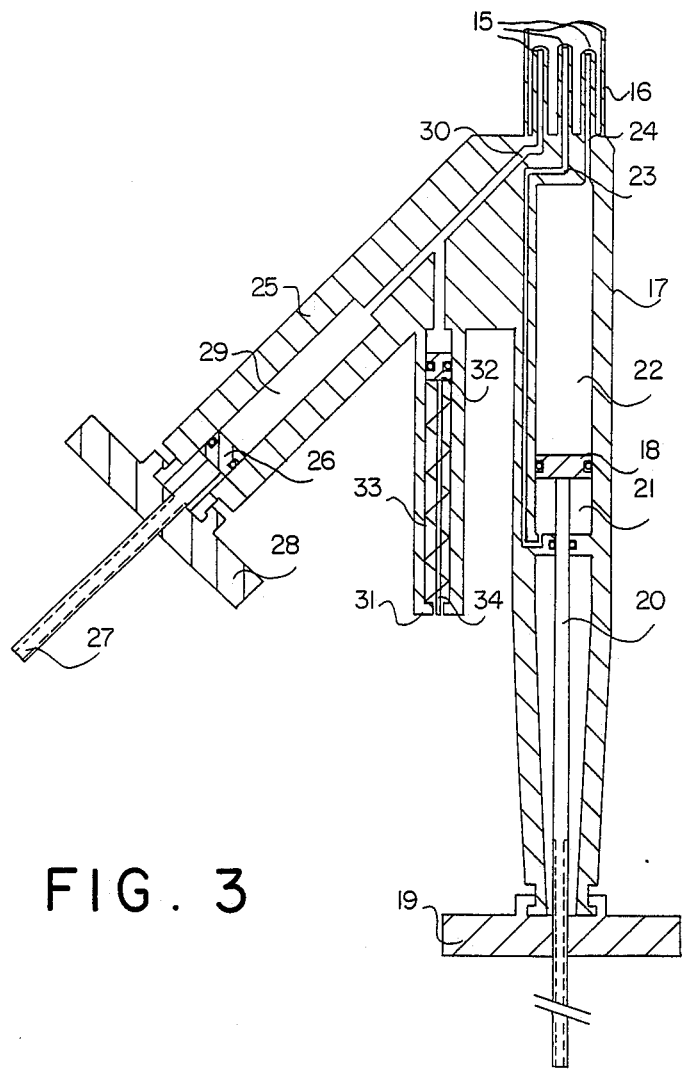
FIG. 3 is a longitudinal section of the part corresponding to the control system C.

Making reference to the above mentioned figures, the device consists of the suturing and cutting head assembly, which has been labelled with the letter A in FIG. 1 and featured in a sectional view in FIG. 2, as well as a flexible body with hydraulic fluid tubes, labelled B in FIG. 1 and partially featured in a sectional view in FIGS. 2 & 3, and finally the control mechanism for operating the approximation/separation of the ends, stapling and cutting of the superfluous tissue, corresponding to the part labelled C in FIG. 1 and featured in a sectional view in FIG. 3.

Head assembly A comprises cylinder (1), inside which there is a double action plunger (2) attached to a shaft (3); the other end of the same shaft, around which is knotted the tissue to be anastomized, is coupled to the support head (4), against which are folded the staples. Said staples are housed in recesses (5) arranged in two concentric rings. They are expelled by the teeth of a pushing comb (6)—which also contains the cutting blade (7)—when the comb is pushed by a second plunger (8) located behind it.

On either side of the double action plunger there are two chambers (9 & 10), which can be filled alternately to achieve the separation and approximation of the support head.

The chambers (9 & 10) and the double action plunger (2) are crossed longitudinally by two thin rigid tubes (11 & 12) which carry the hydraulic fluid to the closing chamber (10) of the support head and to the pushing chamber (13) of the stapling plunger (8); these fine tubes cross the the double action cylinder (2), preventing it, and hence the support head (4), from rotating. A third hydraulic conduction tube (14) leads to the opening chamber (9) of the support head.

The cylinders and chambers are provided with sealing devices, represented in he diagram by toroidal gaskets, but any other system could likewise be employed.

As regards the flexible body B, this is made up of three flexible hydraulic conducting tubes (15) which link up at one end each with the ends of the rigid tubes (11, 12 & 14). These flexible tubes are covered by a plastic tube (16), which is also flexible. At the other end the tubes join up with the control system C, where they receive hydraulic fluid.

Since the set of tubes in body B are flexible, this enables the head to interact with otherwise difficult to reach recesses in the body, and also permits access through the body's natural orifices.

Control system C comprises a cylinder (17), along the inside of which moves a double action plunger (18), screw operated by means of a handwheel (19), which causes its shaft (20) to move. The double action plunger (18) has on either side two hydraulic chambers (21 & 22) which, by means of the outlet tubes (23 & 24) are linked through the flexible tubes in the central body to the head chambers (9 & 10) respectively, in such a way that, upon shutting the back chamber (21), the chamber (10) on head A fills up, causing the support head to close in on the tissue, and on moving the plunger in the opposite direction, fluid from the chamber (22) displaces the plunger (2) of the head, causing the support head (4) to separate, due to the filling of the chamber (9); the fluid of the alternate chambers is evacuated and forced in by moving the handwheel. The length of the shaft (20) which is protruding provides an indication of the degree of approximation of the support head (4).

The surface area of the control plunger (18) may be greater or smaller than the surface areas of the plunger at the head (2), which consequently varies the length of the control device and the effort needed, according to the different requirements.

The control system C comprises the driving mechanism for the staples, which consists of a cylinder (25), inside which is housed a plunger (26) driven by a shaft (27) screwed onto a handwheel (28) which, on being turned, causes the the fluid inside the hydraulic chamber (29) to be pushed out through a tube (30) and up to the head A, into it through tube (12) up to chamber (13), and push the plunger (8) which drives the comb (6) that carries out the stapling and cutting operations. To ensure control over the stapling process, control system C features an optional device in the form of a valve, which comprises a cylinder (31), inside which is housed a plunger (32), one side of which is in contact with the the stapling fluid, and the other side is subject to the pressure of a spring (33), which pressure is slightly higher than that needed for stapling; once stapling has been performed the excess pressure in the chamber (29) obtained by means of the handwheel (28) pushes the plunger (32) of the reservoir or valve, causing the excess fluid to be taken in; this makes the shaft (34) move out, thus giving an indication that the stapling process has been carried out.

Control system C is equipped with the corresponding sealing elements, represented in the diagram by toroidal gaskets, although any other sealing device could also be used, the same as for the head.

I claim:

1. Hydraulic device with flexible body for surgical anastomosis, comprising a suturing and cutting head equipped to receive metal staples and a cylindrical blade, by means of which, driven by hydraulic fliud, the tissue is brought into close contact, sutured and the superfluous tissue cut off; a hydraulically driven control mechanism for the operation of said head; an intermediate body linking the head and control mechanism, including flexible hydraulic fluid tubes; the hydraulic device being hydraulically operated without spring means located in the suturing and cutting head or intermediate body, and said intermediate body, made up of tubes, being sufficiently flexible to enable it to bend in order to facilitate the positioning of the head itself.

2. Hydraulic device with flexible body for surgical anastomosis, in accordance with claim 1, with the feature that the suturing and cutting head carries out the approximation of the tissues to be sutured, as well as stapling and inner cutting of same by means of plungers located in cylinder chambers driven by hydraulic fluid, one of the plungers contained in a double action cylinder chamber which drives hydraulic fluid when axially moved for the approximation and separation of the support head, and another plunger for pushing teeth which force out the staples to their final position, as well as pushing the blade for cutting superfluous tissue, both plungers having sealing means.

3. Hydraulic device with flexible body for surgical anastomosis, in accordance with claim 2, with the feature of having thin hydraulic conduction tubes which carry the hydraulic fluid between the suturing and cutting head and the flexible intermediate body, traversing the plunger contained in the double action cylinder located in the suturing and cutting head, thus avoiding the rotation of the same.

4. Hydraulic device with flexible body for surgical anastomosis, in accordance with claim 2, with the feature that the control mechanism is comprised of hydraulic fluid driving cylinders and plungers, one of the hydraulic fluid driving cylinders being double action and acting upon hydraulic fluid when its plunger is axially moved, and the operation of which by means of a handwheel screwed onto the shaft of the plunger located in the double action driving cylinder allows the approximation and separation of the support head of the head assembly, the position of the plunger's shaft located in the double action driving cylinder being an indication of the degree of the closeness of the tissue, and another plunger whose action, independent of the former plunger, produces the hydraulic pressure for stapling and cutting of the tissue; the surface ratio between the double action plungers located at the suturing and cutting head and at the control mechanism and the screw mechanism for moving the double action plunger in the suturing and cutting head allowing the operations to be carried out with little physical effort.

5. Hydraulic device with flexible body for surgical anastomosis, in accordance with claim 2, with the feature of having a valve in the control mechanism connected to the stapling hydraulic circuit which absorbs the excess pressure in said circuit, and indicating by its displacement that the stapling and cutting have been performed correctly.

6. Hydraulic device with flexible body for surgical anastomosis, in accordance with claim 1, with the feature of having thin hydraulic conduction tubes which carry the hydraulic fluid between the suturing and cutting head and the flexible intermediate body, traversing plunger contained in a double action cylinder located in the suturing and cutting head, thus avoiding the rotation of the same.

7. Hydraulic device with flexible body for surgical anastomosis, in accordance with claim 6, with the feature that the control mechanism is comprised of hydraulic fluid driving cylinders and plungers, one of the hydraulic fluid driving cylinders being double action and acting upon hydraulic fliud when its plunger is axially moved, and the operation of which by means of a handwheel screwed onto the shaft of the plunger located in the double action driving cylinder allows the approximation and separation of the support head of the head assembly, the position of the plunger's shaft located in the double action driving cylinder being an indication of the degree of the closeness of the tissue, and another plunger whose action, independent of the former plunger, produces the hydraulic pressure for stapling and cutting of the tissue; the surface ratio between the double action plungers located at the suturing and cutting head and at the control mechanism and the screw mechanism for moving the double action plunger in the suturing and cutting head allowing the operations to be carried out with little physical effort.

8. Hydraulic device with flexible body for surgical anastomosis, in accordance with claim 6, with the feature of having a valve in the control mechanism connected to the stapling hydraulic circuit which absorbs the excess pressure in said circuit, and indicating by its displacement that the stapling and cutting have been performed correctly.

9. Hydraulic device with flexible body for surgical anastomosis, in accordance with claim 1, with the feature that the control mechanism is comprised of hydraulic fluid driving cylinders and plungers, one of the hydraulic fluid driving cylinders being double action and acting upon hydraulic fluid when its plunger is axially moved, and the operation of which by means of a handwheel screwed onto the shaft of the plunger located in the double action driving cylinder allows the approximation and separation of the support head of the head assembly, the position of the plunger's shaft located in the double action driving cylinder being an indication of the degree of the closeness of the tissue, and another plunger whose action, independent of the former plunger, produces the hydraulic pressure for stapling and cutting of the tissue; said suturing and cutting head including a double action cylinder and plunger; the surface ratio between the double action plungers located at the suturing and cutting head and at the control mechanism and the screw mechanism for moving the double action plunger in the suturing and cutting head allowing the operations to be carried out with little physical effort.

10. Hydraulic device with flexible body for surgical anastomosis, in accordance with claim 9, with the feature of having a valve in the control mechanism connected to the stapling hydraulic circuit which absorbs the excess pressure in said circuit, and indicating by its displacement that the stapling and cuttting have been performed correctly.

11. Hydraulic device with flexible body for surgical anastomosis, in accordance with claim 1, with the feature of having a valve in the control mechanism connected to the stapling hydraulic circuit which absorbs the excess pressure in said circuit, and indicating by its displacement that the stapling and cutting have been performed correctly.

* * * * *